US011298101B2

(12) United States Patent
Amoh et al.

(10) Patent No.: US 11,298,101 B2
(45) Date of Patent: Apr. 12, 2022

(54) DEVICE EMBEDDED IN, OR ATTACHED TO, A PILLOW CONFIGURED FOR IN-BED MONITORING OF RESPIRATION

(71) Applicant: THE TRUSTEES OF DARTMOUTH COLLEGE, Hanover, NH (US)

(72) Inventors: Justice Amoh, Hanover, NH (US); Jeffrey A. Bernowski, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 17/272,610

(22) PCT Filed: Aug. 29, 2019

(86) PCT No.: PCT/US2019/048826
§ 371 (c)(1),
(2) Date: Mar. 1, 2021

(87) PCT Pub. No.: WO2020/047264
PCT Pub. Date: Mar. 5, 2020

(65) Prior Publication Data
US 2021/0244377 A1    Aug. 12, 2021

Related U.S. Application Data

(60) Provisional application No. 62/726,146, filed on Aug. 31, 2018.

(51) Int. Cl.
*A61B 5/00*   (2006.01)
*A61B 7/00*   (2006.01)
*A61B 5/08*   (2006.01)

(52) U.S. Cl.
CPC ............ *A61B 7/003* (2013.01); *A61B 5/0024* (2013.01); *A61B 5/0823* (2013.01);
(Continued)

(58) Field of Classification Search
CPC ..... A61B 7/003; A61B 5/7264; A61B 5/4803; A61B 5/0024; A61B 5/6892;
(Continued)

(56) References Cited

U.S. PATENT DOCUMENTS 5,879,313 A    3/1999  Raviv et al.
6,208,963 B1   3/2001  Martinez et al.
(Continued)

FOREIGN PATENT DOCUMENTS

WO    WO 2017/141317 A1    8/2017

OTHER PUBLICATIONS

International Patent Application No. PCT/US2019/048826, International Search Report and Written Opinion dated Nov. 19, 2019, 21 pgs.

*Primary Examiner* — May A Abouelela
(74) *Attorney, Agent, or Firm* — Lathrop GPM LLP

(57) ABSTRACT

A monitoring device has microphones, an ADC; a digital radio; and a processor with firmware. The firmware includes code for digitizing audio from the microphones into time-domain audio, performing FFT to provide frequency-domain audio, running a first neural network on time domain and frequency-domain audio to extract features, executing a classifier on the features to identify candidate events, and using the digital radio to upload candidate events and features. A pressure sensor awakens the processor from a low-power state. In particular embodiments, the first neural network is an embedded Gated Recurrent Unit having weights trained to extract features of use in the classifier; and candidate events include normal inhalation and exhalation breathing sounds, crackles, wheezes, coughs, snoring, gasping, choking, and speech sounds and in some embodiments (Continued)

heart sounds. A method of monitoring breathing during sleep includes attaching the device to, or embedding the device within, a pillow.

18 Claims, 3 Drawing Sheets

(52) U.S. Cl.
CPC .......... *A61B 5/0826* (2013.01); *A61B 5/4803* (2013.01); *A61B 5/6892* (2013.01); *A61B 5/7257* (2013.01); *A61B 5/7264* (2013.01); *A61B 2560/0214* (2013.01); *A61B 2562/0247* (2013.01)

(58) Field of Classification Search
CPC ... A61B 5/0823; A61B 5/7257; A61B 5/0826; A61B 2560/0214; A61B 2562/0247
USPC ......................................................... 600/586
See application file for complete search history.

(56) References Cited

U.S. PATENT DOCUMENTS

| | | |
|---|---|---|
| 2006/0212273 A1 | 9/2006 | Krausman et al. |
| 2009/0147965 A1 | 6/2009 | Kuo |
| 2011/0034831 A1* | 2/2011 | Christensen ............. A61B 7/04 600/586 |
| 2011/0087079 A1 | 4/2011 | Aarts |
| 2012/0310115 A1* | 12/2012 | Bedingham ............. A61B 5/002 600/586 |
| 2013/0144190 A1* | 6/2013 | Bruce .................. A61B 5/0002 600/586 |
| 2014/0066808 A1* | 3/2014 | Sako ........................ A61B 7/00 600/586 |
| 2014/0188006 A1* | 7/2014 | Alshaer .................. A61B 7/003 600/586 |
| 2014/0194780 A1* | 7/2014 | Alshaer ................ A61B 5/7282 600/586 |
| 2014/0303521 A1* | 10/2014 | Nakamura ............. A61B 7/003 600/586 |
| 2014/0323919 A1* | 10/2014 | Tsutsumi ............. A61B 5/4818 600/586 |
| 2014/0336537 A1* | 11/2014 | Patel ...................... A61B 7/003 600/586 |
| 2014/0350355 A1* | 11/2014 | Aisic ........................ A61B 7/04 600/301 |
| 2015/0025417 A1* | 1/2015 | Schmidt ................. G16H 40/67 600/586 |
| 2015/0073306 A1* | 3/2015 | Abeyratne ............. A61B 5/742 600/586 |
| 2015/0119741 A1* | 4/2015 | Zigel ..................... A61B 7/003 600/529 |
| 2015/0173671 A1* | 6/2015 | Paalasmaa ........... A61B 5/7282 600/301 |
| 2015/0196269 A1* | 7/2015 | Rajan ....................... A61B 7/04 600/586 |
| 2015/0230751 A1* | 8/2015 | Yamanaka ............. A61B 5/742 600/586 |
| 2015/0245788 A1* | 9/2015 | Schmidt ................. G16H 50/30 600/586 |
| 2015/0313484 A1* | 11/2015 | Burg ...................... A61B 5/021 600/301 |
| 2015/0342519 A1* | 12/2015 | Zheng .................. A61B 5/4818 600/586 |
| 2016/0029963 A1* | 2/2016 | Hyde ..................... A61B 7/003 600/301 |
| 2016/0095570 A1* | 4/2016 | Allessie ............ A61B 5/02055 600/301 |
| 2016/0095571 A1* | 4/2016 | Shams ................. A61B 8/0866 600/586 |
| 2017/0113057 A1* | 4/2017 | Goodall ............. A61N 1/37247 |
| 2017/0135632 A1* | 5/2017 | Franceschetti ....... A61B 5/7271 |
| 2017/0360363 A1* | 12/2017 | Fonseca ................ G16H 40/63 |
| 2018/0242918 A1* | 8/2018 | Kogure ................ A61B 5/7221 |
| 2019/0046794 A1* | 2/2019 | Goodall ............... A61N 1/0456 |
| 2019/0167186 A1* | 6/2019 | Mlynczak ........... A61B 5/4818 |
| 2019/0289409 A1* | 9/2019 | Greenberg .......... H04R 25/604 |
| 2020/0015709 A1* | 1/2020 | Peltonen ............. A61B 5/6898 |
| 2020/0178887 A1* | 6/2020 | Correa Ramirez .. A61B 5/4806 |
| 2020/0196942 A1* | 6/2020 | Ozturk .................. A61B 5/747 |

* cited by examiner

Mattress 310

DEVICE EMBEDDED IN, OR ATTACHED TO, A PILLOW CONFIGURED FOR IN-BED MONITORING OF RESPIRATION

CROSS-REFERENCE TO RELATED APPLICATIONS

The present application is a 35 U.S.C. § 371 filing of International Application No. PCT/US2019/048826 filed Aug. 29, 2019, which claims priority to U.S. Provisional Patent Application No. 62/726,146 filed Aug. 31, 2018, the entire contents of which are incorporated herein by reference.

BACKGROUND

In the US alone, an estimated 150 million of people suffer from chronic diseases, including 42 million people suffering from chronic respiratory diseases (including asthma, chronic bronchitis, chronic obstructive pulmonary disease (COPD), and sleep apnea) and 5.8 million people suffering from heart failure.

The severity of these chronic disease can fluctuate and progress over time. Between regularly scheduled doctor's visits and tests, patients often experience exacerbations and acute decompensations. These exacerbations and acute decompensations are common, are traumatic for patients, can result in hospitalization and even death, and are costly for the healthcare system. Monitoring a patient's symptoms and signs can lead to a better understanding of a patient's disease, which can enable better disease management, improved healthcare outcomes, and reduced healthcare costs.

The patient burden of chronic diseases is high, and patients often struggle to adhere to their treatment and monitoring regimen. Monitoring devices, such as blood-pressure cuffs, peak-flow meters, and spirometers, all require that a patient not only remember to perform their monitoring but also put in effort to perform their monitoring correctly.

Wrist-worn accelerometers, such as provided in "Fitbit"-style devices, and optical plethysmographic devices, offer more passive monitoring and may be used to provide some monitoring functions during sleep. These devices, however, do not directly monitor breathing.

It is known that lung and/or heart sounds produced by individuals differ between those produced during normal health and during episodes symptomatic of respiratory and cardiovascular diseases such as asthma, chronic obstructive pulmonary disease (COPD), pneumonia, cystic fibrosis and congestive heart failure; physicians doing physical examinations typically listen to these lung and heart sounds though a stethoscope.

SUMMARY

In an embodiment, a device configured for monitoring physiological sounds includes at least one microphone coupled to an analog-to-digital converter (ADC); a digital radio; and a processor configured with firmware in a memory. The firmware includes machine readable code for using the ADC to digitize audio from the at least one microphone into digitized time-domain audio, performing a fast Fourier transform on the digitized time-domain audio to provide frequency-domain audio, executing a first neural network on the digitized time-domain audio and the frequency-domain audio to extract features from the audio and at least one pressure sensor, executing a classifier on the features to identify candidate events, and using the digital radio to upload the candidate events and features. The at least one pressure sensor is coupled to awaken the processor from a low-power state. In particular embodiments, the first neural network is an embedded Gated Recurrent Unit (e-GRU) having weights trained to extract features of use in the classifier. In particular embodiments, the candidate events include one or more of normal inhalation and exhalation breathing sounds, crackles, wheezes, coughs, snoring, gasping, choking, and speech sounds. In particular embodiments, the candidate events include heart sounds.

In an embodiment, a method of monitoring breathing during sleep includes attaching to a pillow, or embedding within a pillow, a breathing monitor device; extracting features from sound recorded with the breathing monitor device; classifying the extracted features to detect candidate events; and uploading the candidate events with the extracted features and a timestamp.

DETAILED DESCRIPTION OF THE EMBODIMENTS

Figure 1:
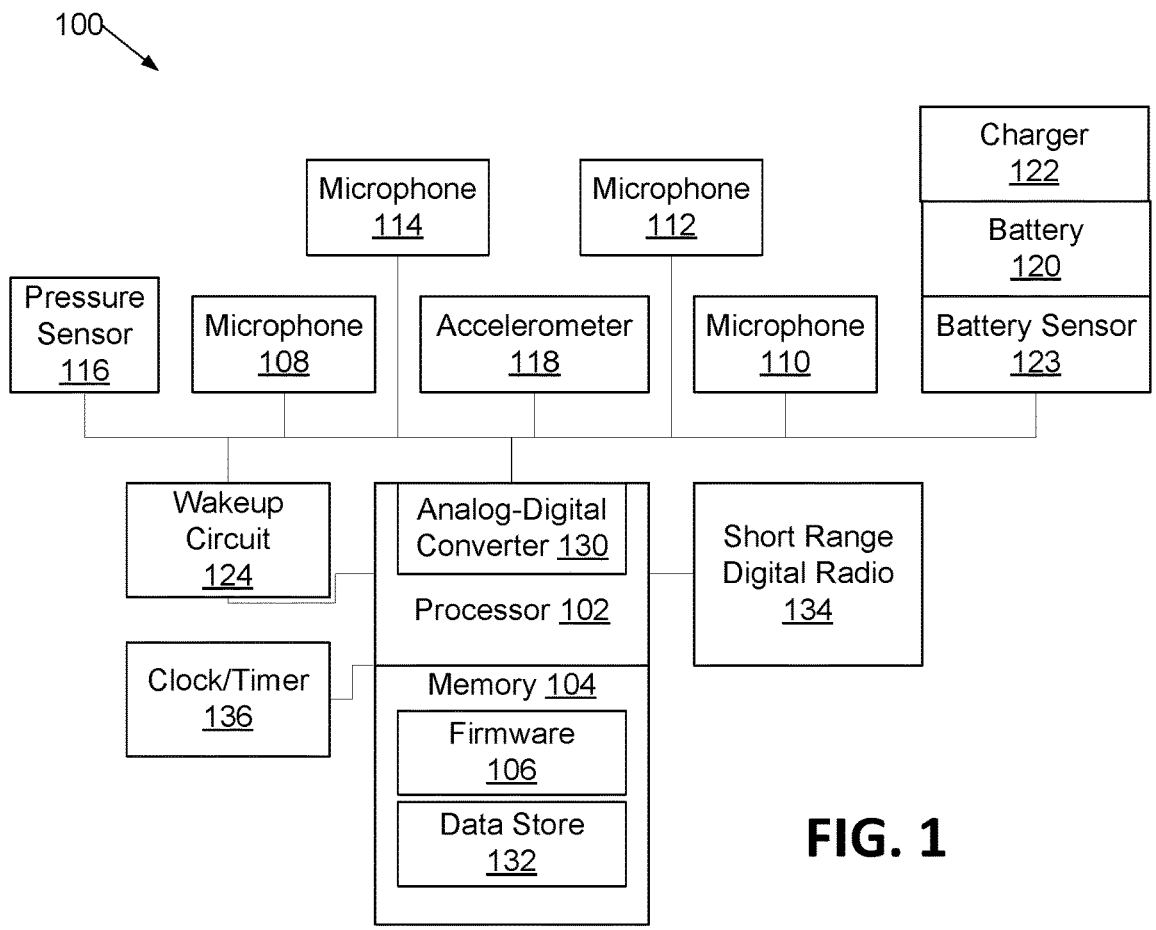
FIG. 1 is a block diagram of a device for monitoring breathing sleep and adapted to be installed within a pillow.

A sleep and breathing monitor device 100 (FIG. 1) has a low power processor 102 with a memory 104 containing machine readable instructions of firmware 106. The device also has at least one, and, in particular embodiments, an array of, microphones 108, 110, 112, 114 or piezoelectric transducers adapted to monitor breath sounds. In embodiments, the device also has one or more pressure sensors 116 and accelerometers 118. The device is powered by a battery 120; battery 120 is in a particular embodiment coupled to be recharged by a charger 122 and has a battery voltage sensor 123 or charge monitor. The sensors, including battery voltage sensor 123, microphones 108, 110, 112, 114, pressure sensor 116, and accelerometers 118 are coupled through analog front-end circuitry (not shown) to the processor 102 and are configured to be read through an analog-to-digital converter 130. Some, but in embodiments not all, of the sensors, including at least one microphone 108 and pressure sensor 116, also couple to provide signals to a wakeup circuit 124 adapted to arouse the processor 102 from a standby state to an operating state when the sensors coupled to it detect conditions indicating that the sleep and breathing monitor is in use for monitoring sleep. Memory 104 also contains a data store 132 configured to hold signatures of interesting sleep events, and processor 102 is coupled to a low-powered digital radio transceiver 134 through which the signatures of interesting sleep events may be transmitted to a smart wireless-equipped device such as a cell phone, tablet computer, or body area network server, for transmission to a server; in a particular embodiment digital radio transceiver 134 is a Bluetooth compatible digital radio. Processor 102 is also coupled to a clock/timer circuit 136.

The microphones 108, 110, 112, 114 are adapted to record breath sounds as well as other physiological sounds such as heart sounds, beats and murmurs. Firmware 106 is configured to extract features from recorded sounds and to classify those features to determine events potentially of interest, these features are stored in data store 132 until they are uploaded.

Figure 2:
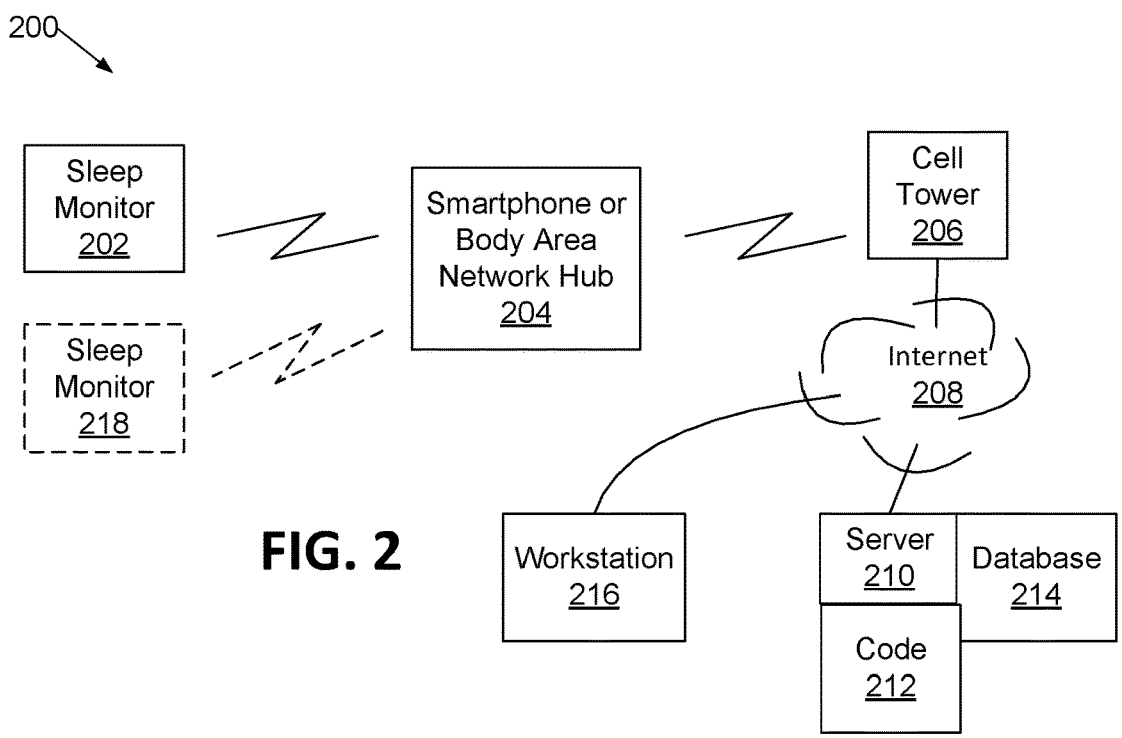
FIG. 2 is a block diagram of a system incorporating the device of FIG. 1.

In an embodiment of a system 200 (FIG. 2) using the sleep and breathing monitor device 100, 202 herein described, the device 202 periodically uses digital radio transceiver 134 to upload the extracted features of breathing and other events classified as potentially of interest from memory 132, in some embodiments with timestamps from clock/timer 136, via a compatible digital radio, such as a Bluetooth radio, into a wireless-equipped smart device 204 such as a smartphone, tablet computer, cell-capable smart watch, or body area network (BAN) hub. The smart device 204 then relays these extracted features, classifications, and timestamps through a cell phone tower 206 or Wi-Fi hotspot and internet 208 to a server 210 where event classification and statistical analysis code 212 in server memory processes the extracted features and preliminary classifications to identify events of interest and compiles relevant statistics. The events of interest and relevant statistics may in embodiments include length and duration of sleep, frequency and length of cessation of breathing during sleep, snoring, gasping snorting and similar episodes during snoring as may occur during obstructive sleep apnea, wheezing as may occur in asthma or chronic obstructive pulmonary disease (COPD), crackles as may occur in pneumonia or congestive heart failure, surges in heart rate indicative of stress, and wakeful spells including time and duration of subject arousal such as when subjects rise to urinate; these events of interest and statistics are recorded in database 214. A user or physician may use a smartphone, tablet computer, or workstation 216 through internet 208 and server 210 to access database 214 to view logs of these events of interest and statistics to better diagnose breathing and sleep-related issues with a user or patient. In some embodiments, an optional second sleep and breathing monitor device 218 may be provided to provide better monitoring of one user, or to monitor two users sharing a bed.

Figure 3:
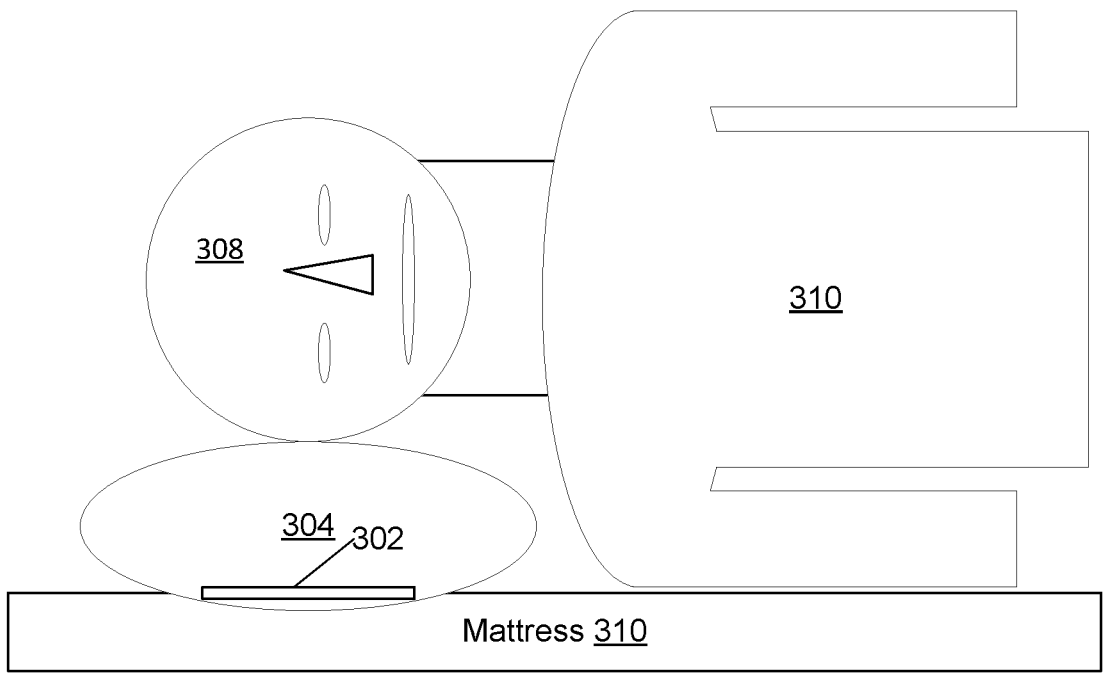
FIG. 3 is an illustration of the device of FIG. 1 positioned in a pillow.
Figure 4:
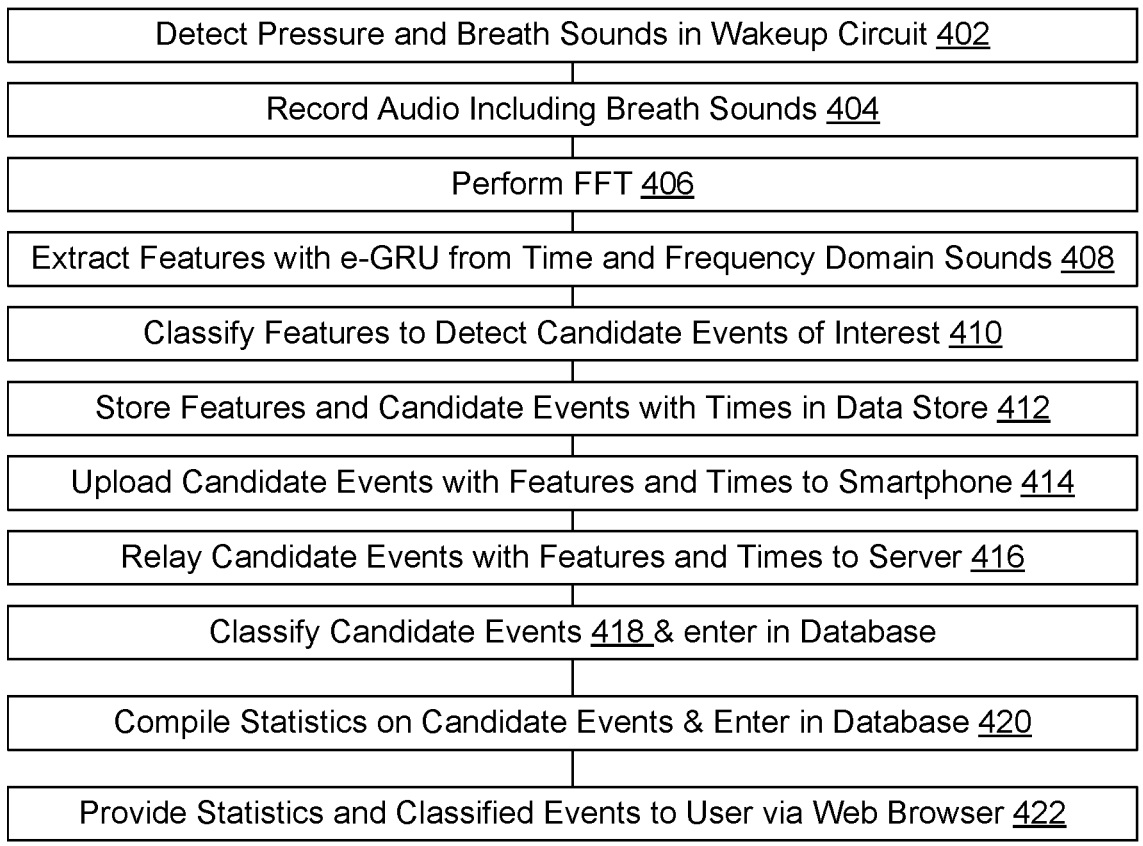
FIG. 4 is a flowchart illustrating a method for monitoring breathing during sleep.

The device is either embedded within foam or another pillow material of a pillow, or designed as an accessory to be attached to a pillow. For instance, when configured as an accessory, the device can take the form of an electronic/smart pillow case for use with standard pillows, or as an electronic pad 302 (FIG. 3) placed beneath a standard pillow 304 in a pillow case. When a user rests his/her head 308 on pillow 304, weight of the head is detected 402 (FIG. 4) by pressure sensor 116, and breathing sounds from head 308 and chest 310 are detected by microphones 108, 110, 112, 114; pressure detection signals and breathing sound signals from pressure sensor 116 and microphones 108, 110, 112, 114 trigger wakeup circuit 124 to arouse processor 102 from a standby state. In a particular embodiment, wakeup circuit 124 arouses or wakes up the processor upon detecting pressure on pressure sensor 116. In an alternative embodiment, wakeup circuit 124 arouses processor 102 from a standby state upon detecting a combination of pressure on pressure sensor 116 and sounds on microphones 108, 110, 112, or 114 that exceed a sound-level threshold.

Figure 5:
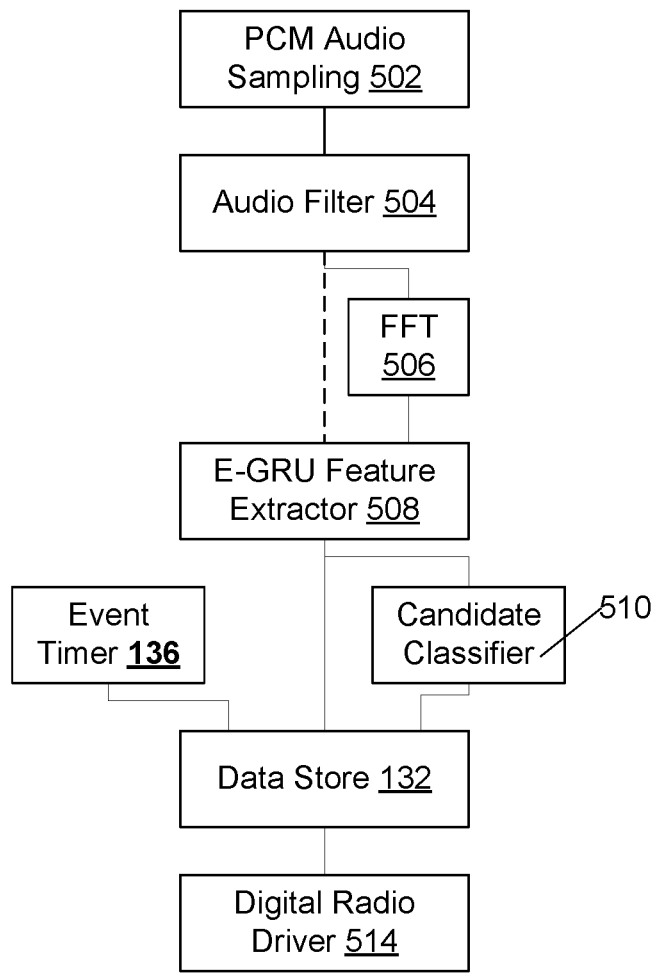
FIG. 5 is a block diagram illustrating firmware on the device for monitoring breathing during sleep.

Once the processor is wakened from the standby state, an audio sampler module 502 (FIG. 5) of the firmware 106 running on processor 102 uses ADC 130 to digitize and record 404 audio in pulse-code modulation (PCM) time-domain form, in some embodiments firmware 106 includes digital audio filtering 504 and downsampling before further processing. A FFT module 506 of firmware 106 then performs 406 a fast Fourier transform (FFT) to transform the PCM time-domain audio into a frequency-domain representation and an e-GRU simulated neural network module 508 extracts 408 features from the frequency-domain representation and in some embodiments from also the PCM time-domain audio. A neural network classifier 510 then detects 410 candidate events and sounds of interest, if no such candidate events and sounds of interest are detected in a timeout interval the processor 102 may revert to a low-power state after uploading any data in data store 132.

Candidate events as classified, together with the features on which their classification was based by classifier 510 and a timestamp from clock timer 136, are stored 412 in data store 132; since features are stored but not PCM audio or the frequency-domain representation of audio, data recorded during speech is generally unintelligible to a listener. Periodically, data, including timestamps, candidate events, and the features on which the candidate events are based, in data store 132 are uploaded 414 by a short-range digital radio driver module 514 of firmware 106 using digital radio 134 to a smart device 204 (FIG. 2) such as a smartphone or other BAN hub, which then relays 416 the data over a network, which may be the internet, to server 210. Code 212 of server 210 then reclassifies 418 candidate events based on the features on which candidate events were based into final detected events. In embodiments, the final detected event classifications include normal inhalation and exhalation breathing sounds, crackles, wheezes, coughs, snoring, gasping and choking, normal heart sounds, tachycardic heart sounds, speech, and arousal. Code 212 also compiles statistics based upon the detected events including respiratory rate, heart rate, and inspiratory-expiratory ratio as well as frequency of wheezes and coughs.

Code 212 enters 420 both detected events and statistics based on the detected events into database 214. When accessed by a smartphone, tablet computer, or a workstation running either a web browser or a specific application, code 212 provides 422 the events and statistics from database 214 to users.

In an embodiment, events in PCM time-domain form and frequency domain representation are classified 410 to detect candidate events by candidate classifier 510 by a e-GRU neural-network classifier trained on a large dataset of sounds previously classified manually. The e-GRU neural network, is an embedded Gated Recurrent Unit (e-GRU) is based on GRUs as defined in Cho, K., Bengio, Y., et al (2014). *Learning Phrase Representations using RNN Encoder-Decoder for Statistical Machine Translation*. In Proc. EMNLP 2014. The e-GRU is redesigned to meet the resource constraints of low power micro-controllers with three key modifications: 1) a single gate mechanism, 2) 3-bit exponential weight quantization and 3) solely fixed-point arithmetic operations. These modifications lead to enormous reductions in memory and computation requirements in e-GRU compared to prior GRUs.

A single gate mechanism modification for the GRU leads to a significant reduction in parameters and computation. An e-GRU cell definition is provided below.

$z_t = \text{softsign}(W_z \odot [h_{t-1}, x_t])$ update gate
$h_t = (1-z_t)*h_{t-1} + z_t * \tilde{h}_t$ cell state
$z_t = (\text{softsign}(W_z \odot [h_{t-1}, x_t])$ update gate
$\tilde{h}_t = (\text{softsign}(W_h \odot [h_{t-1}, x_t]) + 1)/2$ candidate state
$h_t = (1-z_t)*h_{t-1} + z_t * \tilde{h}_t$ cell state Besides the singe gate mechanism, the e-GRU also employs an aggressive 3-bit exponential quantization for the weights. Weight quantization is not new and previous studies have demonstrated that low precision neural networks perform well [4]. In practice, however, 8-bit quantization is typically used in low resource applications. In [5], it was found that while binarization of weights hurts the performance of GRU models, whereas a form of exponential quantization, pow2-ternarization, only suffers a small reduction in accuracy. In e-GRU, we explored this further by investigating exponential quantization in tandem with the single gate optimization. We found that using septenary weights (3-bits, 7 levels) was effective for e-GRU. Furthermore, since the quantized levels were negative integer exponents of 2, this process eliminated the need for weight multiplications (bit shifting is used instead) drastically reducing computation time of an e-GRU cell in processors lacking multiply hardware. A single e-GRU cell requires only 2 bytes of memory, 12 times smaller than needed for a full precision GRU.

Finally, e-GRU uses fixed point arithmetic for fast execution on low power microcontrollers that have no hardware Floating Point Unit. We found the Q15 fixed point format was effective. All operations within the e-GRU network are undertaken in the Q15 format. For the activation functions, integer approximations to the softsign are used which feature left-shifts, additions and division in Q15. As alluded to above, weight multiplications are performed using left-shift operations since all weights are negative integer exponents of 2. Intermediary products are clipped to remain in Q15 format. The summation of multiple e-GRU nodes is, however, allowed to overflow to 32 bits since it is constrained to [−1,1] range by the Q15 activations that ensue. From our simulations, we discovered that all inputs to an e-GRU network flow through the entire model in Q15 format and result in an output that is precise to at least 2 decimal places compared to those from an equivalent full precision network.

In all, e-GRU performs comparably with GRU and thus can enable robust acoustic event detection on an ultra-low power wearable device.

Combinations

The features herein described may be combined in various ways in embodiments anticipated by the inventors. Among embodiments anticipated by the inventors are:

A device designated A configured for monitoring physiological sounds includes at least one microphone coupled to an analog-to-digital converter (ADC); a digital radio; and a processor configured with firmware in a memory. The firmware includes machine readable code for using the ADC to digitize audio from the at least one microphone into digitized time-domain audio, performing a fast Fourier transform on the digitized time-domain audio to provide frequency-domain audio, executing a first neural network on the digitized time domain audio and the frequency-domain audio to extract features from the audio and at least one pressure sensor, executing a classifier on the features to identify candidate events, and using the digital radio to upload the candidate events and features. The at least one pressure sensor is coupled to awaken the processor from a low-power state.

A device designated AA including the device designated A wherein the first neural network is an embedded Gated Recurrent Unit (e-GRU) having weights trained to extract features of use in the classifier.

A device designated AB including the device designated A or AA wherein the classifier is a second neural network.

A device designated AC including the device designated A, AA, or AB wherein the at least one pressure sensor is coupled to awaken the processor through a wake-up circuit, the wake-up circuit also coupled to the at least one microphone.

A device designated AD including the device designated A, AA, AB, or AC wherein the at least one microphone is a plurality of microphones.

A device designated AE including the device designated A, AA, AB, AC, or AD wherein the candidate events comprise normal inhalation and exhalation breathing sounds, crackles, wheezes, coughs, and snoring.

A device designated AF including the device designated A, AA, AB, AC, AD, or AE wherein the candidate events comprise gasping, choking, and speech sounds.

A device designated AG including the device designated A, AA, AB, AC, AD, AE, or AF wherein the candidate events further comprise heart sounds.

A device designated AH including the device designated A, AA, AB, AC, AD, AE, AF, or AG embedded within or attached to a pillow.

A system designated B including the device configured for monitoring of physiological sounds designated A, AA, AB, AC, AD, AE, AF, AG, or AH; and a smart device such as a smartphone, tablet computer, smartwatch, or BAN hub, configured to receive the uploaded candidate events and features from the digital radio.

A system designated BA including the system designated B further including code configured to classify and perform statistical analysis on the candidate events and features, the candidate events being classified into events comprising normal inhalation and exhalation breathing sounds, crackles, wheezes, coughs, and snoring.

A system designated BB including the system designated BA or B wherein the smart device is configured to relay the candidate events and features to a server, the code configured to classify and perform statistical analysis on the candidate events and features being executable on a server.

A method of monitoring breathing during sleep designated C includes attaching to a pillow, or embedding within a pillow, a sleep and breathing monitor device; extracting features from sound recorded with the sleep and breathing monitor device; classifying the extracted features to detect candidate events; and uploading the candidate events with the extracted features and a timestamp.

A method designated CA including the method designated C wherein extracting features from the sound is performed by performing a fast Fourier transform to generate a frequency domain representation of the time domain sound, and using a first neural network on both the time domain sound and the frequency domain representation to extract the features.

A method designated CB including the method designated CA or C wherein the classifying is performed with a second neural network.

Changes may be made in the above system, methods or device without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A device configured for monitoring physiological sounds comprising:
at least one microphone coupled to an analog-to-digital converter (ADC);

a digital radio;

a processor configured with firmware in a memory, the firmware comprising machine readable code configured to:

use the ADC to digitize audio signals from the at least one microphone into digitized time-domain audio signals, perform a fast Fourier transform on the digitized time-domain audio signals to provide frequency-domain audio signals, execute a first neural network on at least the frequency-domain audio signals to extract features from the frequency-domain audio signals and at least one pressure sensor, execute second neural network configured to classify events on the features to identify candidate events, and use the digital radio to upload the candidate events and features;

where the at least one pressure sensor is coupled through a wake-up circuit configured to awaken the processor.

2. The device of claim 1 wherein the first neural network is an embedded Gated Recurrent Unit (e-GRU) having weights trained to extract the features from the frequency domain audio signals for the second neural network.

3. The device of claim 2 wherein the second neural network is a second e-GRU neural network.

4. The device of claim 1 wherein the wake-up circuit is also coupled to the at least one microphone.

5. The device of claim 1 wherein the at least one microphone is a plurality of microphones.

6. The device of claim 1 wherein the candidate events comprise normal inhalation and exhalation breathing sounds, crackles, wheezes, coughs, and snoring.

7. The device of claim 6 wherein the candidate events further comprise gasping, choking, and speech sounds.

8. The device of claim 7 wherein the candidate events further comprise heart sounds.

9. The device of claim 8 being embedded within, or attached to, a pillow.

10. A system comprising:

the device configured for monitoring of physiological sounds of claim 1; and a smart device configured to receive the uploaded candidate events and features from the digital radio, the smart device being selected from the group consisting of a body-area network (BAN) hub, a smartphone, a cellular-capable smartwatch, and a tablet computer.

11. The system of claim 10 further comprising code configured to classify and perform statistical analysis on the candidate events and features, the candidate events being classified into events comprising normal inhalation and exhalation breathing sounds, crackles, wheezes, coughs, and snoring.

12. The system of claim 11 wherein the first neural network is an embedded Gated Recurrent Unit (e-GRU) having weights trained to extract the features for the second neural network.

13. The device of claim 12 wherein the second neural network is a second e-GRU neural network.

14. The system of claim 11 wherein the smartphone is configured to relay the candidate events and features to a server, the server configured to classify and perform statistical analysis on the candidate events and features being executable on the server.

15. The device of claim 2 wherein the candidate events comprise normal inhalation and exhalation breathing sounds, crackles, wheezes, coughs, and snoring.

16. The device of claim 3 wherein the candidate events comprise normal inhalation and exhalation breathing sounds, crackles, wheezes, coughs, and snoring.

17. The device of claim 4 wherein the candidate events comprise normal inhalation and exhalation breathing sounds, crackles, wheezes, coughs, and snoring.

18. The device of claim 5 wherein the candidate events comprise normal inhalation and exhalation breathing sounds, crackles, wheezes, coughs, and snoring.

* * * * *